United States Patent [19]

Okazaki et al.

[11] Patent Number: 4,849,441
[45] Date of Patent: Jul. 18, 1989

[54] ISOINDOLIN-1-ONE DERIVATIVE AND ANTIARRHYTHMIC AGENT

[75] Inventors: Kei Okazaki, Machida; Etsuo Oshima, Shizuoka; Hiroyuki Obase, Shizuoka; Yoshimasa Oiji, Shizuoka; Masaaki Nito, Shizuoka; Kazuhiro Kubo, Shizuoka, all of Japan

[73] Assignee: Kyowa Hakko Kogyo Co., Ltd., Tokyo, Japan

[21] Appl. No.: 136,855

[22] Filed: Dec. 22, 1987

[30] Foreign Application Priority Data

Dec. 25, 1986 [JP] Japan .................................. 61-307802

[51] Int. Cl.$^4$ ..................... A61K 31/40; C07D 209/46
[52] U.S. Cl. .................... 514/414; 514/278; 514/318; 514/323; 514/339; 514/416; 546/15; 546/201; 546/273; 548/410; 548/465; 548/472
[58] Field of Search ........................ 548/472, 410, 465; 546/15, 201, 273; 514/416, 323, 414, 339, 278, 409

[56] References Cited

U.S. PATENT DOCUMENTS

| | | | |
|---|---|---|---|
| 3,091,568 | 5/1963 | Bub ..................... | 548/472 |
| 3,445,476 | 5/1969 | Sulkowski et al. ................... | 548/472 |
| 3,538,113 | 11/1970 | Houlihan ............................ | 548/472 |
| 3,849,570 | 11/1974 | Raschack et al. ..................... | 514/416 |
| 3,885,037 | 5/1975 | Sulkowski ........................... | 514/400 |
| 4,087,541 | 5/1978 | Eberlein et al. ..................... | 514/411 |

FOREIGN PATENT DOCUMENTS 1229652 4/1971 United Kingdom .

OTHER PUBLICATIONS

A. Knoll, Chem. Abstracts, vol. 58, No. 1412h (1962).
J. Sprague et al., Chem. Abstracts, vol. 68, No. 114434d (1968).
Arch. Int. Pharmacodyn. Ther., 185, 47 (1970); C. Hanna "Gitan, 2-(β-Diethylaminoethyl)-3-Phenylphthalimidine Phosphate an Antitussive Agent".
Chemical Abstracts, vol. 76, No. 1, 1,18, Jan. 3, 1972, Columbus, Ohio, U.S.A. and related Sulkowski, et al. "Tetrahydropyrimidinyl- and Imidazolinylphenyl Ketones as Antidepressants and Diuretics", p. 346, col. 1, 2, Abstract-No. 3 893y.
Chemical Abstracts, vol. 83, No. 23,1,18, Dec. 8, 1975, Columbus, Ohio, U.S.A. and related Sulkowski, Theodore S. "Producing Anorexia Using Imidazolinyl Phenyl Carbonyl Compounds, Their Acid Addition Salts and Related Compounds", p. 473, col. 2, Abst. No. 193 362q.
Chemical Abstracts, vol. 72, No. 19, May 11, 1970, Columbus, Ohio, U.S.A. and related Houlihan, William J., "2-(2-Amino-ethyl)-3-(substitutedphenyl)-phthalimidines", p. 354, col. 1, Abstract No. 100 505y.
Chemical Abstracts, vol. 87, No. 1, 1,18 Jul. 4, 1977, Columbus, Ohio, U.S.A. and related Thomae, Dr. Karl, GmbH "Substituted arylalkylamines", p. 630, col. 1, Abstract-No. 23 039e.

*Primary Examiner*—Mary E. Ceperley
*Attorney, Agent, or Firm*—Antonelli, Terry & Wands

[57] ABSTRACT

Isoindolin-1-one compounds represented by the following formula (I);

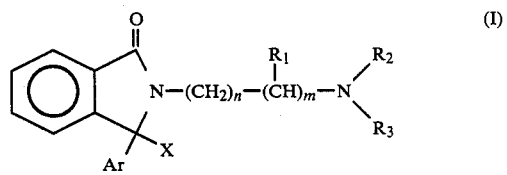

{wherein n represents an integer of 1 to 6; m represents 0 or 1; $R_1$, $R_2$ and $R_3$ are each independently hydrogen or lower alkyl, and when m is 1, $R_1$ and one of $R_2$ and $R_3$ may form a five-membered or six-membered ring over N atom; X represents hydrogen or hydroxy; Ar represents naphthyl, pyridyl or substituted phenyl represented by the formula (II); Ar and X may form a lactone ring;

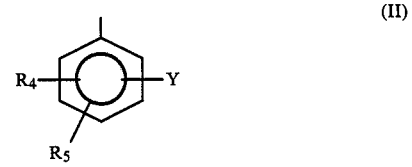

[wherein Y represents carboxyl, lower alkoxycarbonyl, carbamoyl, N,N-lower alkyl-substituted carbamoyl or amino represented by the formula (III):

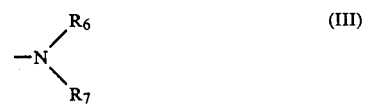

(wherein $R_6$ and $R_7$ are each independently hydrogen, lower alkyl or lower alkanoyl); $R_4$ and $R_5$ are each independently hydrogen, lower alkyl, cyano or halogen]} or a pharmaceutically acceptable acid addition salt or metal salt thereof have an excellent antiarrhythmic activity.

17 Claims, No Drawings

ISOINDOLIN-1-ONE DERIVATIVE AND ANTIARRHYTHMIC AGENT

BACKGROUND OF THE INVENTION

The present invention relates to isoindolin-1-one derivatives and antiarrhythmic agents comprising the same as an effective ingredient.

It is known that 2-(N,N-dialkyl-substituted aminoalkyl)-3-phenylisoindolin-1-one derivatives are used as the local anesthesia and antispasmodic or antitussive agents [U.S. Pat. No. 3,091,568; Arch. Int. Pharmacodyn. Ther., 185, 47 (1970)]. In the patent supra, a halogen atom, a hydroxy group, a lower alkyl group and a lower alkoxy group are mentioned as the substituent of the 3-phenyl group, but none of a carboxyl group, a carbamoyl group and an amino group is mentioned.

It is also disclosed that 2-(N,N-diethylaminoethyl)-3-phenylisoindolin-1-one is used as an antiarrhythmic agent (U.S. Pat. No. 3,849,570).

Novel compounds having an excellent antiarrhythmic activity, especially those having less side effects are always in demand.

SUMMARY OF THE INVENTION

According to the present invention, an isoindolin-1-one compound represented by the formula (1);

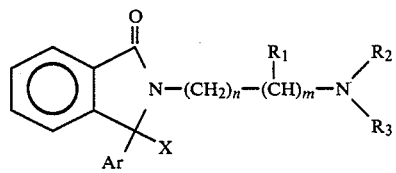
(I)

{wherein n represents an integer of 1 to 6; m represents 0 or 1; $R_1$, $R_2$ and $R_3$ are independently hydrogen or lower alkyl, and when m is 1, $R_1$ and one of $R_2$ and $R_3$ may form a five-membered or six-membered ring over N atom; X represents hydrogen or hydroxy; Ar represents naphthyl, pyridyl or substituted phenyl represented by the formula (II); Ar and X may form a lactone ring;

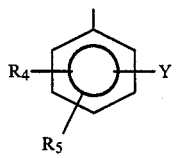
(II)

[wherein Y represents carboxyl, lower alkoxycarbonyl, carbamoyl, N,N-lower alkyl-substituted carbamoyl or amino represented by the formula (III):

(III)

(wherein $R_6$ and $R_7$ are independently hydrogen, lower alkyl or lower alkanoyl); $R_4$ and $R_5$ are independently hydrogen, lower alkyl, cyano or halogen]} [hereinafter referred to as Compound (1), and compounds with other formula numbers are hereinafter likewise referred to] or a pharmaceutically acceptable acid addition salt or metal salt thereof and an antiarrhythmic agent comprising at least one of these compounds as an effective component are provided.

DETAILED DESCRIPTION OF THE INVENTION

In definitions of the respective groups in formula (I), as the lower alkyl, an alkyl group having 1 to 6 carbon atoms such as methyl, ethyl, propyl, etc. is mentioned. Examples of the halogen include a fluorine atom, a chlorine atom, a bromine atom and an iodine atom. As the lower alkanoyl, an alkanoyl group having 1 to 6 carbon atoms such as formyl, acetyl, propionyl, butyryl, etc. is mentioned.

Compound (I) includes all of possible steric isomers.

Next, processes for producing compound are described below.

(1) Compound (I) wherein

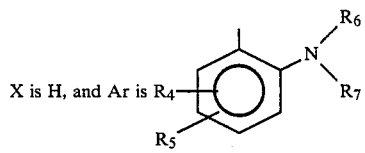

X is H, and Ar is can be produced by the following process.

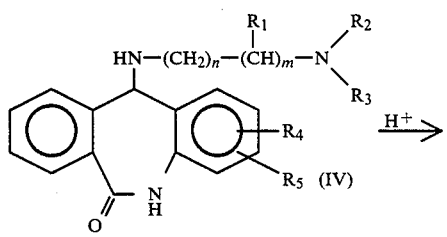
(IV)

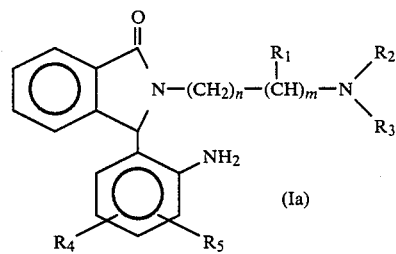
(Ia)

wherein $R_1$ to $R_5$, m and n are as previously defined.

Compounds (IV) is reacted under acidic conditions to obtain Compound (Ia). As the acid, mineral acids such as hydrochloric acid, sulfuric acid, phosphoric acid, etc., organic acids such as acetic acid, fumaric acid, etc., Lewis acids such as zinc chloride, boron trifluoride, etc. can be employed in an amount of 0.1 to 10 equivalents based on Compound (IV) as a starting material. The reaction is carried out at an appropriate temperature from room temperature to 100° C. in a solvent such as water, an alcohol, dimethylformamide, chloroform, acetonitrile, etc. and completed in 30 minutes to 12 hours.

A process for producing the compound (IV) used as the starting material is described below;

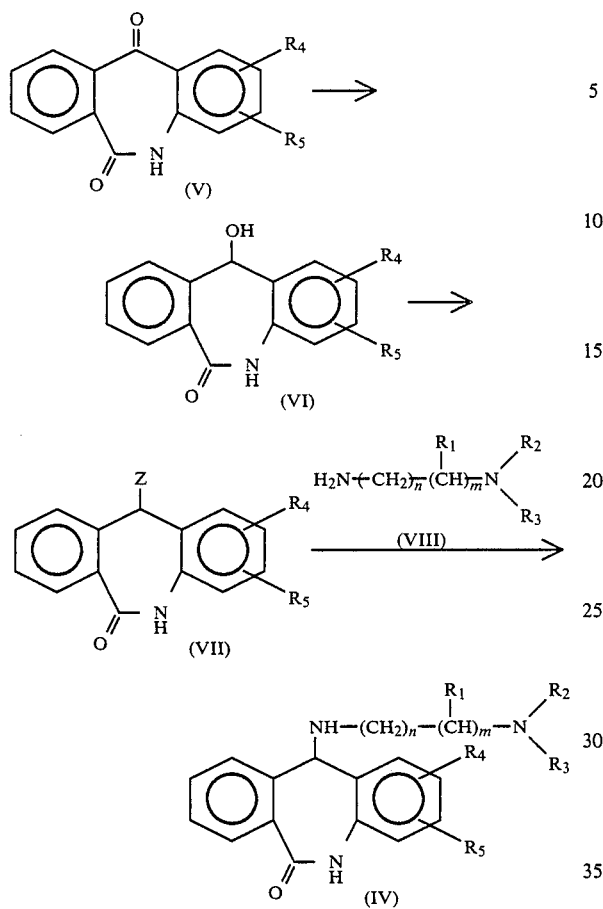

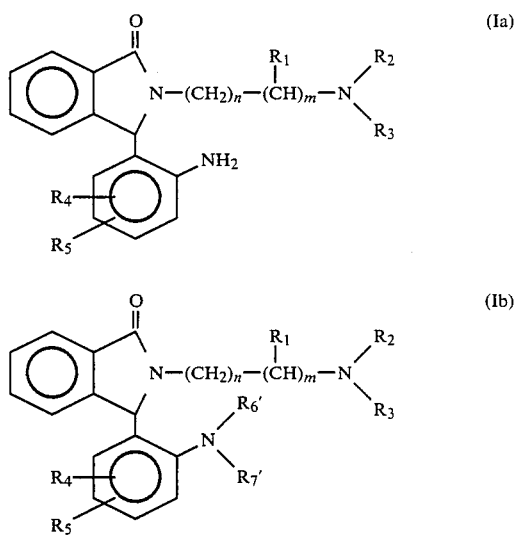

wherein $R_1$ to $R_5$, m and n are as previously defined and Z represents a halogen atom.

Compound (IV) can be obtained by reducing Compound (V), halogenating Compound (VI) and then reacting, Compound (VII) with Compound (VIII) in a conventional manner [Belgian Pat. No. 637802 (1964)].

For example, Compound (V) is reacted with 1 to 10 equivalents of sodium borohydride at an appropriate temperature from 0° to 50° C. in a solvent such as methyl alcohol, ethyl alcohol, etc. for an hour to overnight. The solvent is distilled away, and the resulting Compound (VI) is reacted with 1 to 10 equivalents of a halogenating agent, for example, thionyl chloride, phosphorus oxychloride, phosphorus pentachloride, hydrogen bromide, phosphorus tribromide, etc. in an inert solvent, for example, a solvent such as N,N-dimethylformamide, toluene, chloroform, dichloromethane, tetrahydrofuran, etc. at an appropriate temperature of 0° to 100° C. for 30 minutes to overnight. The solvent is distilled away, and the resulting Compound (VII) wherein Z is chlorine atom or bromine atom is reacted with Compound (VIII) at an appropriate temperature from 0° to 100° C. in a solvent such as N,N-dimethylformamide, toluene, chloroform, dichloromethane, tetrahydrofuran, methyl alcohol, ethyl alcohol, etc. for 30 minutes to overnight to obtain Compound (IV).

Among Compound (V) used as the starting material, compounds wherein $R_4$ and $R_5$ are a hydrogen atom, a cyano group and a halogen atom are commercially available and known materials [for example, Japanese Published Unexamined Patent Application No. 119481/79, U.S. Pat. No. 3,354,147 (1965), J. Pharm. Pharmacol., 21, 520 (1969), etc.]. Further, with respect to compound (V) wherein $R_4$ and $R_5$ are a lower alkyl group, Compound (VII) wherein Z is lower alkoxy can be produced in a conventional manner [Tetrahedron Letters, 21, 173 (1980)], and therefore Compound (IV) can likewise be obtained by reacting Compound (VII) with Compound (VIII). A specific example of the preparation is shown in Reference Example (1).

Next, Compound (Ia) is subjected to reductive amination in a conventional manner [J. Am. Chem. Soc., 93, 2897 (1971)] to obtain Compound (Ib):

wherein $R_1$ to $R_5$, m and n are as previously defined; $R_{6'}$ represents a lower alkyl group and $R_{7'}$ represents a hydrogen atom or a lower alkyl group.

An aldehyde or ketone is reacted with Compound (Ia) and the product is subjected to chemical reduction using sodium cyanoborohydride, etc. or catalytic reduction to give Compound (Ib).

Compound (Ia) is reacted with 1 to 20 equivalents of an aldehyde or a ketone under neutral to acidic conditions in an inert solvent such as benzene, toluene, methylene chloride, ethanol, etc. at an appropriate temperature of 0° C. to the boiling point of solvent for approximately 10 minutes to 2 hours. The reaction may be carried out in the presence of a dehydrating agent such as anhydrous magnesium sulfate, molecular sieves, etc. Then, the formed Schiff's base is reacted with 1 to 20 equivalents of sodium cyanoborohydride at 0° C. to room temperature for 1 to 24 hours to give Compound (Ib). Compound (Ib) can also be obtained by stirring the Schiff's base in a hydrogen atmosphere in the presence of a catalyst such as palladium carbon, Raney nickel, etc.

Next, Compound (Ia) is reacted with an activated acylating agent such as an acid anhydride, etc. to give Compound (Ic).

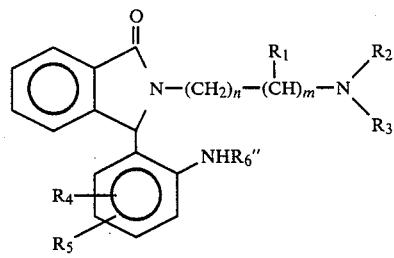
(Ic)

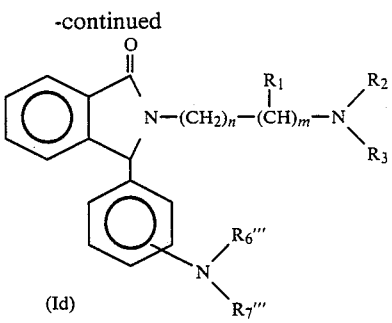
(Id)

wherein R₁ to R₅, m and n are as previously defined; and $R_6''$ represents a lower alkanoyl group.

The acid anhydride or acid halide is reacted with Compound (Ia) in a solvent such as chloroform, dimethylformamide, pyridine, etc. at a temperature of 0° C. from the boiling point of the solvent in the presence of a base such as triethylamine, pyridine, etc. The reaction is completed in 10 minutes to 24 hours.

(2) The Compound (I) wherein

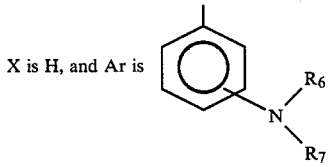

X is H, and Ar is is prepared by the following process.

wherein R₁ to R₃, m and n are as previously defined and; $R_6'''$ and $R_7'''$ each represent a lower alkyl group. Compound (XI) and Compound (XII) are prepared from Compound (IX) and Compound (X) in a conventional manner [cf. Tetrahedron Letters, 5103 (1978)].

For example, a solution of Compound (X) in tetrahydrofuran or ether is dropwise added at −78° C. to a solution of Compound (IX), which is prepared from N,N-diethylbenzamide and 1 equivalent of sec-butyl lithium at −78° C. in tetrahydrofuran or ether in the presence of at least 1 equivalent of N,N,N′,N′-tetramethylethylenediamine. The temperature is gradually elevated to 0° C., and the reaction mixture is allowed to stand at 0° C. for an hour to overnight to give a mixture of Compound (XI) and Compound (XII).

Compound (XI) and Compound (XII) may be separated from each other and then independently reacted with Compound (VIII). Alternatively, the mixture of Compound (XI) and Compound (XII) may also be reacted with Compound (VIII).

Compound (XI) and Compound (XII) are reacted with 1 to 20 equivalents of Compound (VIII) in the absence of any solvent or in an inert solvent such as dioxane, N,N-dimethylformamide, toluene, etc. in the presence of a catalytic amount of a Lewis acid, for example, zinc chloride, stannic chloride, ferric chloride, etc. at an appropriate temperature from room temperature to 200° C. for 1 to 5 hours to give Compound (Id).

The Compound (X) is commercially available and readily accessible.

(3) Compound (Ie) wherein Ar′ is naphthyl group, pyridyl group or N,N-lower alkyl-substituted carbamoyl-substituted phenyl and X is OH and Compound (If) wherein Ar′ is as previously defined and X is H are prepared by the following process:

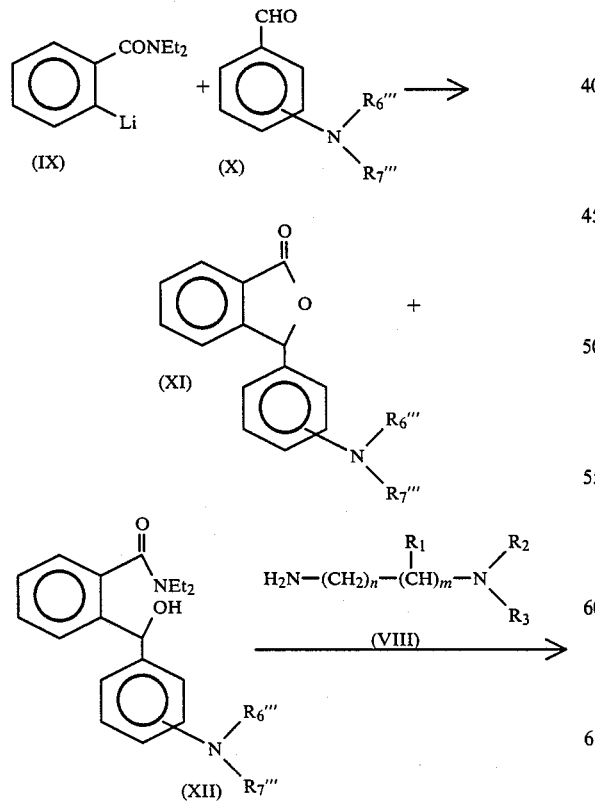

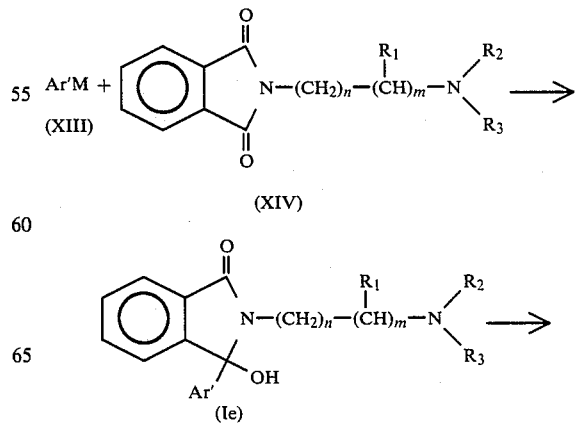

-continued

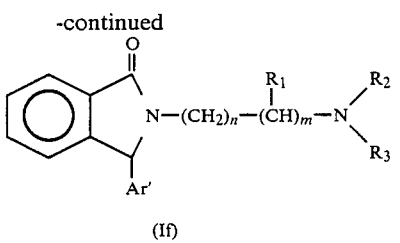

(If)

wherein M represents a magnesium halide or a lithium atom; Ar' represents naphthyl group, pyridyl group or N,N-lower alkyl-substituted carbamoyl-substituted phenyl; and $R_1$ to $R_3$, m and n are as previously defined.

Compound (Ie) is prepared from Compound (XIV) and compound (XIII) prepared in a conventional manner [Rec. Trav. Chim., 70, 1054 (1951)] by a known method [J. Pract. Chem., 30, 204 (1965)].

A proportional ratio of Compound (XIII) to Compound (XIV) is optional; it is generally advantageous to use Compound (XIII) and Compound (XIV) in equimolar amounts. Compound (XIII) is reacted with Compound (XIV) in an inert solvent such as cyclohexane, diethyl ether, tetrahydrofuran, benzene, ethyleneglycol dimethyl ether, etc. at an appropriate temperature from −78° C. to the boiling point of the solvent for 30 minutes to overnight to give Compound (Ie).

Compound (XIV) can be readily prepared by the method described in J. Am. Chem. Soc., 68, 1657 (1946).

Compound (If) can be obtained from Compound (Ie) in accordance with the known method (J. Chem. Soc., Perkin I, 1975, 1574). Compound (If) can also be obtained by treating Compound (Ie) with zinc.

For example, Compound (Ie) wherein Ar' is naphthyl, or carboxy-substituted phenyl is reacted with 1 to 20 equivalents of zinc powders previously activated with hydrochloric acid in acetic acid at an appropriate temperature from room temperature to the boiling point of the solvent for an hour to overnight to give Compound (If) wherein Ar' is naphthyl or carboxy-substituted phenyl.

Compound (If) wherein Ar' is pyridyl can be obtained by converting Compound (Ie) wherein Ar' is pyridyl into Compound (XV):

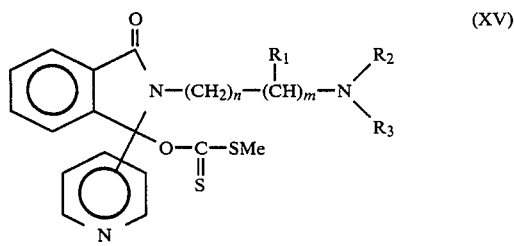

(XV)

wherein $R_1$ to $R_3$, m and n are as previously defined, and then reducing Compound (XV).

The 3-[(methylthio) thiocarbonyloxy] derivative (XV) can be obtained, for example, by reacting compound (Ie) wherein Ar' is pyridyl, in sequence, with a catalytic amount of imidazole and 1 to 3 equivalents of sodium hydride for 10 minutes to an hour in tetrahydrofuran in an inert gas such as nitrogen, argon, etc.; an excess of carbon disulfide for 10 minutes to an hour; and 1 to 2 equivalents of methyl iodide or of dimethyl sulfate for 10 minutes to an hour, at an appropriate temperature from 0° C. to the boiling point of the solvent. By reacting Compound (XV) with 1 to 2 equivalents of tri-n-butyl tin hydride in xylene at a boiling point of the solvent for 10 minutes to an hour to give Compound (If) wherein Ar' is pyridyl.

Further, by treating Compound (Ie) wherein Ar' is ortho-lower alkyl-substituted carbamoyl group under acidic conditions, the corresponding lactone derivative (Ig) can be prepared:

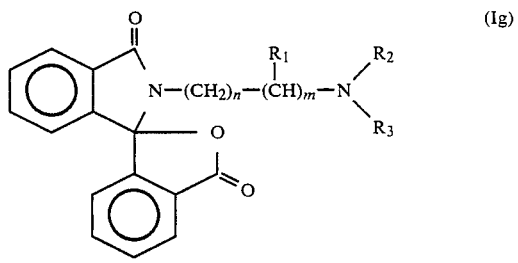

(Ig)

wherein $R_1$ to $R_3$, m and n are as previously defined.

Further, by treating Compound (Ig) with zinc under the conditions described above, Compound (If) wherein Ar' is carboxy-substituted phenyl can be obtained.

Isolation and purification of the compounds (including intermediates) obtained by the processes described above can be performed, unless otherwise specified, by conventional operations ordinarily used in organic synthesis reactions, for example, filtration, extraction with an organic solvent, e.g., ethylacetate, methylene chloride, etc.; drying, concentration and then, if necessary, purification such as recrystallization or column chromatography, and the like.

In the case of producing salts of compound (I), when the product is obtained as a salt, it may be purified as it is; in case that it is obtained as a free form, a salt thereof may be formed in a conventional manner.

As the pharmaceutically acceptable acid addition salt of Compound (I), inorganic salts such as hydrochlorides, sulfates, phosphates, etc.; and organic acid salts such as acetates, maleates, fumarates, tartarates, citrates, etc. may be mentioned; and as the metal salts thereof, alkali metal salts such as sodium salts, potassium salts, etc. and alkaline earth metal salts such as magnesium salts, calcium salts, etc. may be mentioned.

Next, specific examples of the compounds of the present invention, their structures and their physicochemical properties are shown in Tables 1, 2 and 3, respectively.

TABLE 1

1. 3-(2-Aminophenyl)-2-(2-diethylaminoethyl)isoindolin-1-one
2. 3-(2-Aminophenyl)-2-(2-dimethylaminopropyl)isoindolin-1-one
3. 3-(2-Aminophenyl)-2-(3-diethylaminopropyl)isoindolin-1-one
4. 3-(2-Aminophenyl)-2-(4-diethylaminobutyl)isoindolin-1-one
5. 2-(Di-n-butylaminobutyl)-3-(2-aminophenyl)isoindolin-1-one
6. 3-(2-Aminophenyl)-2-(2-isopropylaminoethyl)isoindolin-1-one
7. 2-(2-Diethylaminoethyl)-3-(2-methylaminophenyl)isoindolin-1-one
8. 2-(2-Diethylaminoethyl)-3-(2-dimethylaminophenyl)isoindolin-1-one
9. 2-(2-Diethylaminoethyl)-3-(2-ethylaminophenyl)isoindolin-1-one
10. 3-(2-n-Butylaminophenyl)-2-(2-diethylaminoethyl)isoindolin-1-one
11. 3-(2-Amino-5-chlorophenyl)-2-(2-diethylaminoethyl)-isoindolin-1-one
12. 3-(5-Chloro-2-methylaminophenyl)-2-(2-diethylaminoethyl)-isoindolin-1-one
13. 3-(5-Chloro-2-dimethylaminophenyl)-2-(2-diethylaminoethyl)-isoindolin-1-one TABLE 1-continued 14. 3-(5-Chloro-2-ethylaminophenyl)-2-(2-diethylaminoethyl)-isoindolin-1-one
15. 3-(5-Chloro-2-n-butylaminophenyl)-2-(2-diethylaminoethyl)-isoindolin-1-one
16. 3-(2-Acetamidophenyl)-2-(2-diethylaminoethyl)isoindolin-1-one
17. 3-(2-Amino-3, 6-dimethylphenyl)-2-(2-diethylaminoethyl)-isoindolin-1-one
18. 2-(2-Diethylaminoethyl)-3-(4-dimethylaminophenyl)-isoindolin-1-one
19. 2-(2-Diethylaminoethyl)-3-(4-diethylaminophenyl)isoindolin-1-one
20. 2-(2-Diethylaminoethyl)-3-hydroxy-3-(1-naphthyl)-isoindolin-1-one
21. 2-(2-Diethylaminoethyl)-3-hydroxy-3-(3-pyridyl)isoindolin-1-one
22. 2-(2-Diethylaminoethyl)-3-(3-pyridyl)isoindolin-1-one
23. 2-(2-Diethylaminoethyl)-3-hydroxy-3-(2-pyridyl)isoindolin-1-one
24. 2-(2-Diethylaminoethyl)-3-(2-pyridyl)isoindolin-1-one
25. 3-(2-Amino-3-methylphenyl)-2-(2-diethylaminoethyl)-isoindolin-1-one
26. 3-(2-Amino-3, 5-dimethylphenyl)-2-(2-diethylaminoethyl)-isoindolin-1-one
27. 2-[2-(2-Diethylaminoethyl)isoindolin-1-on-3-yl] benzoic acid
28. 2-(2-Diethylaminoethyl)-3-(2-methoxycarbonylphenyl)-isoindolin-1-one
29. 3-(N,N—Diethylcarbamoylphenyl)-2-(2-diethylaminoethyl)-3-hydroxyisoindolin-1-one
30. Spiro [2-(2-diethylaminoethyl)isoindolin-3-one 1, 1'-1', 3'-dihydroisobenzofuran-3'-one]
31. 3-(2-Amino-5-cyanophenyl)-2-(2-diethylaminoethyl)-isoindolin-1-one
32. 3-(2-Amino-5-fluorophenyl)-2-(2-diethylaminoethyl)-isoindolin-1-one
33. 3-(2-Amino-3-isopropylphenyl)-2-(2-diethylaminoethyl)-isoindolin-1-one
35. 3-(2-Amino-3-cyanophenyl)-2-[(1-ethylpyrrolidin-2-yl)methyl]isoindolin-1-one
36. 3-(2-Amino-5-cyanophenyl)-2-(2-isopropylaminoethyl)-isoindolin-1-one
37. 3-(2-Amino-5-carbamoylphenyl)-2-(2-diethylaminoethyl)-isoindolin-1-one
38. 3-(2-Amino-5-cyanophenyl)-2-(2-ethylaminoethyl)-isoindolin-1-one

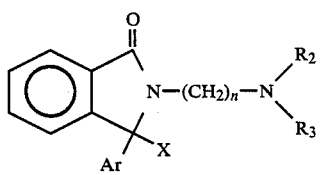

M: $CH_3$
E: $C_2H_5$
i-P: $i-C_3H_7$
n-B: $n-C_4H_9$

In Ar, Ar other than Ar-1 through 4 represents:

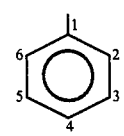

and a substituent(s) of the substituted phenyl group is/are shown in the table wherein a numeral suffix indicates the position of the substituent(s).

Ar-1:

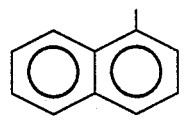

Ar-2:

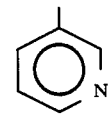

Ar-3:

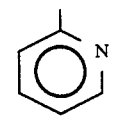

Ar-4: Ar-4 represents, together with X:

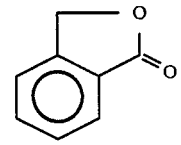

Z:

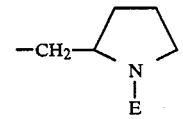

(Z is bound directly to N of the isoindole)

| No. of Compound | n | $NR_2R_3$ | Ar | X |
|---|---|---|---|---|
| 1 | 2 | $NE_2$ | $2NH_2$ | H |
| 2 | 3 | $NM_2$ | " | H |
| 3 | 3 | $NE_2$ | " | H |
| 4 | 4 | " | " | H |
| 5 | 3 | $N-nB_2$ | " | H |
| 6 | 2 | $NHCHM_2$ | " | H |
| 7 | 2 | $NE_2$ | 2NHM | H |
| 8 | 2 | " | $2NM_2$ | H |
| 9 | 2 | " | 2NHE | H |
| 10 | 2 | " | 2NHnB | H |
| 11 | 2 | " | $2NH_2$, 5Cl | H |
| 12 | 2 | " | 2NHM, 5Cl | H |
| 13 | 2 | " | $2NM_2$, 5Cl | H |
| 14 | 2 | " | 2NHE, 5Cl | H |
| 15 | 2 | " | 2NHnB, 5Cl | H |
| 16 | 2 | " | 2NHCOM | H |
| 17 | 2 | " | $2NH_2$, 3M, 6M | H |
| 18 | 2 | " | $4NM_2$ | H |
| 19 | 2 | " | $4NE_2$ | H |
| 20 | 2 | " | Ar-1 | OH |
| 21 | 2 | " | Ar-2 | OH |
| 22 | 2 | " | Ar-2 | H |
| 23 | 2 | " | Ar-3 | OH |
| 24 | 2 | " | Ar-3 | H |
| 25 | 2 | " | $2NH_2$, 3M | H |
| 26 | 2 | " | $2NH_2$, 3M, 5M | H |
| 27 | 2 | " | 2COOH | H |
| 28 | 2 | " | $2CO_2M$ | H |
| 29 | 2 | " | $2CONE_2$ | OH |
| 30 | 2 | " | Ar-4 | H |
| 31 | 2 | " | $2NH_2$, 5CN | H |
| 32 | 2 | " | $2NH_2$, 5F | H |
| 33 | 2 | " | $2NH_2$, $5CHM_2$ | H |

TABLE 1-continued

| No. of Compound | n | NR₂R₃ | Ar | X |
|---|---|---|---|---|
| 35 | — | Z | 2NH₂, 5CN | H |
| 36 | 2 | NHiP | 2NH₂, 5CN | H |
| 37 | 2 | NE₂ | 2NH₂, 5CONH₂ | H |
| 38 | 2 | NHE | 2NH₂, 5CN | H |

1'. Dihydrochloride 0.25 hydrate of Compound 1
2'. Dihydrochloride dihydrate 0.5 methylalcoholate of Compound 2
3'. Dihydrochloride dihydrate of Compound 3
4'. 1.5 Hydrochloride dihydrate of Compound 4
5'. Monohydrochloride dihydrate of Compound 5
6'. Monofumarate of Compound 6
8'. Dihydrochloride monoacetonitrilate of Compound 8
9'. Dihydrochloride 0.8 hydrate of Compound 9
10'. Dihydrochloride 0.5 hydrate of Compound 10
11'. Dihydrochloride 0.5 hydrate of Compound 11
12'. Dihydrochloride of Compound 12
13'. Dihydrochloride of Compound 13
14'. Dihydrochloride of Compound 14
15'. Monohydrochloride 0.5 ethyl alcohol monohydrate of Compound 15
17'. Dihydrochloride 0.33 hydrate of Compound 17
18'. Dihydrochloride 2.4 hydrate of Compound 18
20'. Monohydrochloride 0.4 hydrate of Compound 20
22'. Dihydrochloride of Compound 22
25'. Dihydrochloride 0.6 hydrate of Compound 25
26'. Dihydrochloride dihydrate of Compound 26
31'. Monofumarate monohydrate of Compound 31
31''. Monohydrochloride of Compound 31
32'. Dihydrochloride 1.5 hydrate of Compound 32
33'. Monofumarate 0.5 isopropanol 0.25 hydrate of Compound 33
35'. Monofumarate 1.33 hydrate of Compound 35
36'. Dihydrochloride 0.2 acetonitrile 0.5 hydrate of Compound 36
37'. Dihydrochloride 0.5 hydrate 0.1 isopropanol of Compound 37
38'. Dihydrochloride of Compound 38
38''. Monohydrochloride of Compound 38

TABLE 3

| | IR Spectrum (cm⁻¹) | NMR Spectrum (δppm) Solvent Measured | Melting Point (°C.) | Elemental analysis Upper column calcd (%) Lower column found (%) | | |
|---|---|---|---|---|---|---|
| | | | | C | H | N |
| 1 | (neat) | [CDCl₃] 0.93(t,6H), 2.46(q,4H), 2.22–4.82(m,4H), 3.11–3.56(m,2H), 5.41–6.21(m,1H), 6.21–8.02(m,7H) | Oily | — | | |
| 1' | (KBr disk) 3100–2300, 1680, 1470, 1402, 745 | — | 202–210 | 59.92 59.81 | 6.91 7.03 | 10.48 10.52 |
| 2' | (KBr disk) 3150–2250, 1675, 1475, 1415, 745 | — | 100–110 | 53.92 53.93 | 7.19 7.44 | 9.67 9.92 |
| 3' | (KBr disk) 3100–2150, 1670, 1475, 1415, 745 | — | 110–120 | 56.50 56.87 | 7.45 7.73 | 9.41 9.39 |
| 4 | (KBr disk) 3400, 2960, 1665, 1495, 1460, 1420, 1315, 745 | [CDCl₃] 0.96(t,6H), 1.31–1.97(m,4H), 2.20–4.48(m,8H) 2.97–3.38(m,2H), 5.35–6.05(m,1H), 6.35–8.17(m,7H) | 127–128 | 75.18 75.48 | 8.32 8.64 | 11.95 11.94 |
| 5 | (KBr disk) 3450, 3350, 2950, 1680, 1495, 1470, 1410, 1300, 740, 725 | [CDCl₃] 0.54–2.03(m,14H), 2.04–2.68(m,6H), 2.71–3.39(m,1H), 3.49–4.23(m,1H), 2.96–4.56(m,2H), 5.29–6.01(m,1H), 6.27–7.99(m,8H) | 79.5–82 | 76.30 76.08 | 8.96 9.32 | 10.68 10.59 |
| 6 | (KBr disk) 3400, 3350, 2950, 1660, 1490, 1460, 1405, 1300, 745, 725 | [CDCl₃] 0.98(d,6H), 2.27–4.37(m,5H), 2.88–3.40(m,2H), 5.39–6.24(m,1H), 6.21–8.06(m,8H) | Oily | — | | |
| 6' | (KBr disk) 3100–2250, 1675, 1620, 1470, 1415, 980, 740 | — | 179–180 | 64.93 64.93 | 6.40 6.57 | 9.88 9.75 |
| 7 | (KBr disk) 3390, 2950, 1675, 1465, 1410, 1305, 745, 725 | [CDCl₃] 0.92(t,6H), 2.46(q,4H) 2.93–3.29(m,1H), 2.37–4.38(m,7H), 5.45–6.22(m,1H), 6.23–8.13(m,8H) | 95–100 | 74.74 74.54 | 8.06 8.32 | 12.45 12.37 |
| 8 | (neat) 2970, 1690, 1470, 1405, 1300, 1095, 760, 745, 730 | [CDCl₃] 0.97(t,6H), 2.24–3.48(m,7H), 2.87(brs,6H), 3.56–4.35(m,1H), | Oily | — | | |

TABLE 3-continued

| | IR Spectrum (cm$^{-1}$) | NMR Spectrum (δppm) Solvent Measured | Melting Point (°C.) | Elemental analysis Upper column calcd (%) Lower column found (%) | | |
|---|---|---|---|---|---|---|
| | | | | C | H | N |
| | | 6.28–8.19(m,9H) | | | | |
| 8' | (KBr disk) 3100–2150, 1685, 1460, 1390, 760, 725 | — | 192–195 | 61.93 61.66 | 7.36 7.60 | 12.04 11.92 |
| 9 | (KBr disk) 3400, 2970, 1680, 1610, 1470, 1460, 1415, 750 | [CDCl$_3$] 0.93(t,6H), 0.38–1.71(m,3H), 2.48(q,4H), 2.11–4.54(m,6H), 2.17–3.14(m,1H) 5.49–6.26(m,1H), 6.30–8.13(m,8H) | Solid | — | | |
| 9' | (KBr disk) 3400, 3050–2200, 1680, 1465, 1395, 740, 725 | — | 85–90 | 60.26 60.29 | 7.49 7.77 | 9.58 9.64 |
| 10 | (neat) 3375, 2960, 1680, 1610, 1470, 1410, 1315, 745, 730 | [CDCl$_3$] 0.93(t,6H), 0.50–2.07(m,7H), 2.48(q,4H), 2.12–4.46(m,6H), 2.77–3.52(m,1H), 5.50–6.19(m,1H), 6.28–8.20(m,8H) | Oily | — | | |
| 10' | (KBr disk) 3000–2100, 1680, 1460, 740, 720 | — | 55–65 | 62.46 62.60 | 7.86 8.11 | 9.11 8.95 |
| 11 | (neat) 3350, 3240, 2960, 1680, 1490, 1470, 1405, 1240, 815, 745, 725 | [CDCl$_3$] 0.95(t,6H), 2.50(q,4H), 2.21–4.33(m,4H), 3.11–3.79(m,2H), 5.43–6.21(m,1H), 6.21–8.14(m,7H) | Oily | — | | |
| 11' | (KBr disk) 3100–2100, 1700, 1485, 1470, 1400, 745 | — | 210–216 | 54.74 54.89 | 5.97 6.22 | 9.53 9.53 |
| 12 | (neat) 3400, 2960, 1680, 1510, 1470, 1400, 1360, 1240, 805, 745, 725 | [CDCl$_3$] 0.94(t,6H), 2.49(q,4H), 2.11–4.33(m,7H), 5.49–6.19(m,1H), 6.19–8.04(m,7H) | Oily | — | | |
| 12' | (KBr disk) 3100–2100, 1690, 1470, 1400, 750 | — | 90–100 | 56.70 56.76 | 6.34 6.65 | 9.45 9.28 |
| 13 | (KBr disk) 3400, 2960, 1690, 1490, 1475, 1405, 1115, 735 | [CDCl$_3$] 0.94(t,6H), 2.51(q,4H), 2.16–4.61(m,10H), 6.34(brs,1H), 6.55–8.11(m,7H) | 0.7 hydrate 86–88 | 66.30 66.46 | 0.7 hydrate 7.44 7.37 | 10.54 10.53 |
| 13' | (KBr disk) 3100–1900, 1690, 1490, 1470, 1395, 1120, 740, 730 | — | 178–182 | — | | |
| 14 | (neat) 3480, 2960, 1680, 1510, 1470, 1400, 1305, 1240, 805, 745, 725 | [CDCl$_3$] 0.93(t,6H), 0.48–1.63(m,3H), 2.48(q,4H), 2.13–4.38(m,6H), 5.5–6.2(m,1H), 6.20–8.07(m,7H) | Oily | | | |
| 14' | (KBr disk) 3100–1900, 1690, 1470, 1395, 800, 742, 720 | — | 100–115 | 57.59 57.64 | 6.59 6.90 | 9.16 9.07 |
| 15 | (neat) 3380, 2955, 1680, 1510, 1470, 1400, 1300, 805, 745, 725 | [CDCl$_3$] 0.93(t,6H), 0.45–1.96(m,7H), 2.49(q,4H), 2.15–4.34(m,6H), 2.71–3.14(m,1H), 5.43–6.20(m,1H), 6.24–8.13(m,7H) | Oily | — | | |
| 15' | (KBr disk) 3050–2000, 1685, | — | 60–70 | 61.77 | 7.98 | 8.31 |

TABLE 3-continued

| | IR Spectrum (cm$^{-1}$) | NMR Spectrum (δppm) Solvent Measured | Melting Point (°C.) | Elemental analysis Upper column calcd (%) Lower column found (%) | | |
|---|---|---|---|---|---|---|
| | | | | C | H | N |
| | 1470, 1400, 800, 5, 720 | | | 61.53 | 7.69 | 8.35 |
| 16 | (KBr disk) 3240, 2970, 1660, 1480, 1440, 1420, 1300, 760, 735 | [CDCl$_3$ + DMSO-d$_6$] 0.89(t,6H), 1.95–4.19(m,11H), 5.92(brs,1H), 6.36–7.93(m,8H), 9.89(brs,1H) | 186–187 | 72.30 72.17 | 7.45 7.63 | 11.50 11.55 |
| 17 | (KBr disk) 3470, 3380, 2975, 1660, 1465, 1400 | [CDCl$_3$] 0.94(t,6H), 1.36(s,3H), 2.22(s,3H), 2.51(q,4H), 2.29–3.13(m,2H), 3.46–4.38(m,2H), 4.42(brs,2H), 6.25(s,1H), 6.33 and 6.88 (q,2H,ABtype), 7.00–8.01(m,4H) | 139–140 | 75.18 75.52 | 8.32 8.59 | 11.95 12.17 |
| 17' | (KBr disk) 2950, 1690, 1470, 1400 | — | 160 (decompd.) | 61.40 61.64 | 7.42 7.84 | 9.76 9.53 |
| 18' | (KBr disk) 3050–2100, 1675, 1465, 1400, 720 | 1.26(t,6H), 3.15(brs,6H), 2.67–4.74(m,8H), 6.15(brs,1H), 6.87–8.09(m,8H), 10.76(brs,1H) | 85–95 | 56.50 56.78 | 7.72 8.10 | 8.99 8.64 |
| 19 | (KBr disk) 2960, 1675, 1405, 1355, 785, 740, 705 | [CDCl$_3$] 0.95(t,6H), 1.13(t,6H), 2.50(q,4H), 3.32(q,4H), 2.51–4.22(m,4H), 5.51(s,1H), 6.6 and 6.92 (q,4H,ABtype), 6.40–7.58(m,3H), 7.57–7.96(m,1H) | 63–65 | 75.95 76.15 | 8.76 8.98 | 11.07 11.00 |
| 20 | (KBr disk) 2975, 3150–2000, 1695, 1470, 1380, 1370, 1085, 800, 775, 765 | [CDCl$_3$] 1.01(t,6H), 1.93–4.11(m,8H), 6.73–8.13(m,10H), 8.32–8.73(m,1H), 10.02(brs,1H) | Solid | 76.98 77.18 | 7.00 7.16 | 7.48 7.15 |
| 20' | (KBr disk) 3000–2150, 1700, 1470, 1385, 1070, 795, 765 | — | 130–135 | 68.94 68.95 | 6.70 6.71 | 6.70 6.80 |
| 21 | (neat) 3300–2050, 2980, 1700, 1475, 1380, 1070, 770, 715, 700 | [CDCl$_3$] 1.02(t,6H), 1.98–3.30(m,7H), 3.76–4.31(m,1H), 7.02–8.04(m,6H), 8.44–8.90(m,2H) | Oily | — | — | — |
| 22 | (neat) 2975, 1690, 1475, 1405, 750, 720, 700 | [CDCl$_3$] 0.93(t,6H), 2.47(q,4H), 1.94–4.42(m,4H), 5.78(s,1H), 6.90–8.03(m,6H), 8.32–8.85(m,2H) | Oily | — | — | — |
| 23 | (KBr disk) 3100–2150, 2980, 1700, 1470, 1385, 1315, 1070, 765, 700 | [CDCl$_3$] 1.00(t,6H), 1.87–3.22(m,7H), 3.71–4.27(m,1H), 6.31–7.44(m,1H), 6.94–8.02(m,7H), 8.30–8.61(m,1H) | 86–88 | 70.71 70.61 | 7.17 6.77 | 12.56 12.33 |
| 24 | (neat) 2975, 1695, 1475, 1405, 745 | [CDCl$_3$] 0.90(t,6H), 2.46(q,4H), 2.37–4.39(m,4H), 5.87(s,1H), 6.76–8.07(m,7H), 8.47–8.73(m,1H) | Oily | — | — | — |
| 25 | (neat) 3360, 2960, 1670, 1470, 1405, 1090, 760, 745 | CDCl$_3$] 0.93(t,6H), 2.48(q,4H), 1.89–4.66(m,7H), 2.88–3.38(m,2H), 5.52–6.14(m,1H), 6.21–8.08(m,7H) | Oily | — | — | — |

TABLE 3-continued

| | IR Spectrum (cm$^{-1}$) | NMR Spectrum (δppm) Solvent Measured | Melting Point (°C.) | Elemental analysis Upper column calcd (%) Lower column found (%) | | |
|---|---|---|---|---|---|---|
| | | | | C | H | N |
| 25' | (KBr disk) 3100–2150, 1660, 1470, 1400, 725 | — | 81–83 | 59.88 60.19 | 7.23 7.62 | 9.98 9.99 |
| 26' | (KBr disk) 3150–2150, 1690, 1475, 1400, 750 | [DMSO-d$_6$] (270MHz) 1.18(t,6H), 2.08(s,3H), 2.41(s,3H), 3.01–3.35(m,6H), 3.35–3.50(m,1H), 4.03–4.21(m,1H), 6.76(s,1H), 6.24(d,1H), 7.06(s,1H), 7.46–7.67(m,3H), 7.75–7.85(m,1H) | 60.5–62 β | 57.39 57.42 | 7.66 7.56 | 9.13 9.18 |
| 27 | (KBr disk) 2800–1850, 1680, 1590, 1380, 745 | [CDCl$_3$] 1.30(t,6H), 2.82–4.89(m,8H), 6.35–6.71(m,1H), 6.84–8.12(m,8H), 8.90(brs,1H) | 74.5–100 | 68.09 67.80 | 7.07 7.14 | 7.56 7.52 |
| 28 | (neat) 2975, 1725, 1700, 1280, 1083, 760, 745 | [CDCl$_3$] 0.89(t,6H), 2.44(q,4H), 2.27–3.16(m,4H), 3.95(s,3H), 6.72–8.13(m,9H) | Oily | — | | |
| 29 | (KBr disk) 3450, 2980, 1705, 1635, 1470, 1385, 770, 758 | [CDCl$_3$] (270MHz) 0.68(brs,3H), 0.98(t,6H), 1.06(brs,3H), 1.65(brs,2H), 2.27–2.50(m,2H), 2.50–2.70(m,2H), 2.70–3.10(m,2H), 3.10–3.50(m,2H), 7.00–7.58(m,7H), 7.70–7.85(m,1H) | 128–129 | 70.89 70.92 | 7.85 8.05 | 9.92 9.91 |
| 30 | (KBr disk) 2970, 1780, 1720, 1380, 1095, 920, 770, 760 | [CDCl$_3$] 0.87(t,6H), 2.40(q,4H), 2.19–3.68(m,4H), 6.84–8.18(m,8H), 4.03(d,1H) | 100–102 | 71.98 72.07 | 6.33 6.42 | 7.99 7.96 |
| 31 | (disk) 3360, 3240, 2960, 2220, 1660, 1610, 1505, 1470, 1410, 1315, 730, 700 | [CDCl$_3$] 0.94(t,6H), 2.50(q,4H), 1.98–3.39(m,3H), 3.49–4.28(m,1H), 3.74–4.11(m,2H), 5.14–6.20(m,1H), 6.32–8.10(m,7H) | — | — | | |
| 31' | (KBr disk) 3100–2250, 2225, 1670, 1610, 980 | — | 70–72 (amorphous) | 62.23 62.16 | 6.27 6.38 | 11.61 11.35 |
| 31" | — | — | 229–232 | 65.53 65.46 | 6.55 6.52 | 14.56 14.43 |
| 32 | — | [CDCl$_3$] 0.94(t,6H), 2.50(q,4H), 1.9–3.5(m,5H), 3.5–4.3(m,1H), 5.4–6.3(m,1H), 6.3–8.0(m,7H) | Oily | — | | |
| 32' | — | — | 182–186 | 54.42 54.70 | 6.62 6.93 | 9.52 9.85 |
| 33 | (neat) 3475, 3380, 2970, 1680, 1465, 1410, 750, 720, 710 | [CDCl$_3$] 0.92(t,6H), 0.98–1.51(m,6H), 2.47(q,4H), 2.33–3.39(m,4H), 3.46–4.08(m,1H), 2.97–3.28(m,2H), 5.50–6.15(m,1H), 6.18–8.03(m,7H) | Oily | — | | |
| 33' | (KBr disk) 3100–2250, 1680, 1460, 750 | — | 164–167 | 69.48 69.48 | 8.25 8.13 | 9.17 9.42 |
| 35 | (KBr disk) 3350, 3224, 2966, 2216, 1680, 1607, 1505 | — | — | — | | |

TABLE 3-continued

| IR Spectrum (cm$^{-1}$) | NMR Spectrum ($\delta$ppm) Solvent Measured | Melting Point (°C.) | Elemental analysis Upper column calcd (%) Lower column found (%) | | |
|---|---|---|---|---|---|
| | | | C | H | N |
| 35' (KBr disk) 3210, 2216, 1680, 1607, 1505, 983, 646 | [DMSO-d$_6$] (270MHz) 0.8–1.25(m,3H), 1.4–2.0(m,4H), 2.1–3.4(m,6H), 3.7–3.9(m,1H), 6.11(s,1H), 6.5–6.9(m), 7.30–7.45(m,2H), 7.45–7.65(m,2H), 7.7–7.85(m,1H) | Amorphous | 62.40 62.47 | 6.17 6.39 | 11.19 10.82 |
| 36 (KBr disk) 3354, 3222, 2964, 2216, 1680, 1604, 1507 | — | — | — | | |
| 36' (KBr disk) 2800, 2218, 1690, 1608, 1500, 1471, 1395, 751 | [DMSO-d$_6$] (270MHz) 1.21(t,6H), 2.95–3.4(m,4H), 3.9–4.15(m,1H), 6.39(s,1H), 6.75(d,1H), 6.89(d,1H), 7.30–7.87(m,5H), 8.62–9.05(m,2H) | Hygroscopic | 57.71 57.71 | 6.08 6.16 | 13.86 13.88 |
| 37' — | [DMSO-d$_6$] (270MHz) 1.1–1.3(m,6H), 3.0–3.5(m,7H), 3.9–4.2(m,1H), 6.43(s,1H) 7.0–7.15(m,2H), 7.4–7.9(m,6H) | 218–219.5 | 56.30 56.23 | 6.61 6.41 | 12.33 12.11 |
| 38 (neat) 3354, 3238, 2218, 1662, 1607, 1505, 1409 | [CDCl$_3$] 1.04–1.11(m,3H), 2.58–2.66(m,2H), 2.81–2.86(m,2H), 2.95–3.25(m,1H), 3.78(s,1H), 3.86–4.13(m,1H), 5.52(brs,1H), 5.66, 6.01(s,1H), 6.56–6.78(m,2H), 7.22–7.66(m,5H), 7.91–7.94(d,1H) | Oily | — | | |
| 38' — | — | 192.5–194.5 (decompd.) | 58.02 58.02 | 5.64 5.68 | 14.24 14.10 |
| 38'' — | — | 210–213 | 63.95 63.65 | 5.93 6.01 | 15.70 15.77 |

Next, the antiarrhythmic activity and acute toxicity of the compounds of the present invention are described below.

Antiarrhythmic activity test:

The antiarrhythmic activity was examined by arrhythmia test induced with chloroform in mice and by arrhythmia test induced by ligation of dog coronary artery.

(A) Mice chloroform-induced arrhythmia test:

Using mice of dd strain, weighing 18 to 22 g and fasting and abstaining from water for 4 to 5 hours, an antiarrhythmic effect was evaluated in accordance with the method of Block [Life Science, 28, 2623 (1981)]. That is, after orally administrating each compound, the mice were put in a chloroform atmosphere and taken out after respiratory standstill. Electrocardiogram was measured by the standard limb induction method; in the case when frequent pulse exceeding 720 pulses/min. is continued for 30 seconds or longer, it was judged ineffective and in the case of a heart beat number being less than 720 pulses/min., it was judged effective. ED$_{50}$ was determined by the Probit method. The results are shown in Table 4.

(B) Dog coronary artery ligation-induced arrhythmia test:

Using dogs weighing 7 to 12 kg, coronary artery ligation-induced arryhthmia occurred in accordance with the Harris method [Circulation, 1, 1318 (1950)]. Namely, the left fifth costa was subjected to thoracolaparotomy. After the pericardium was incised, the left fore descending branch of the coronary artery was exfoliated around the first side branch and ligated. Sixteen hours after, a test compound was intravenously administered to dogs with multiple ventricular arrhythmic pulses being 90% or more than the total pulses. Then, electrocardiogram was recorded without anesthesia under free movement, and a case where 50% or more of the total pulses was restored to sinus rhythm was judged effective.

The minimum effective dose (MED) of the drug was made a dose in which the effect was noted in 50% or more cases used. The results are shown in Table 4.

Acute toxicity test:

Groups each consisting of three dd, male mice having body weights of 20±1 g were used, and the compound of the present invention was intraperitoneally administered. Mortality 7 days after the administration was observed and the minimum lethal dosage (MLD) was determined. The results are shown in Table 4.

TABLE 4

| Compound | Acute Toxicity (MLD) (mg/kg) | | Antiarrhythmic Activity (mg/kg) | |
|---|---|---|---|---|
| | p.o. | i.p. | A | B |
| 1' | >300 | >100 | 33 | 1.25 |
| 2' | >300 | >100 | >100 | 5 |
| 3' | 100 | >100 | 100> | 2.5 |
| 4' | 200 | >100 | 47 | 1.25 |
| 5' | 100 | 25 | 35 | 1.25 |
| 6' | 300 | >100 | 36 | 2.5 |
| 7 | 50 | 50 | 14 | >2.5 |
| 8' | 100 | 50 | 36 | 2.5 |
| 9' | 200 | >100 | 63 | >5 |
| 11' | >300 | >100 | >100 | 5 |
| 17' | 300 | >100 | 25> | — |
| 18' | 100 | 50 | 23 | 2.5 |
| 26' | 200 | 100 | 25> | — |
| 31' | >300 | >100 | 30 | 2.5 |
| 31" | >300 | >100 | 19 | 2.5 |
| 32' | 300 | >100 | 25–50 | — |
| 33' | 100 | 50 | 14 | — |
| 35' | >300 | >100 | 50–100 | — |
| 36' | >300 | >100 | 50–100 | — |
| 38' | >300 | >100 | 50 | — |
| 38" | >300 | >100 | 50 | 5 |

A: chloroform-induced arrhythmia in mice ($ED_{50}$)
B: coronary artery ligation-induced arrhythmia in dog (MED)

Compound (I) and pharmaceutically acceptable acid addition salts thereof can be employed in a variety of medicament forms depending upon purposes of administration, in view of the pharmacological activity. The pharmaceutical composition of the present invention can be prepared by uniformly mixing an effective amount of a free Compound (I) or a pharmaceutically acceptable salts thereof as an active component with a pharmaceutically acceptable carrier. The carrier can take a wide range of forms in accordance with a desirable medicament form for the administration. These medicament compositions are desirably in a unit dosage form suitable for the oral administration or injection administration. In the preparation of a composition in the oral dosage form, any useful, pharmaceutically acceptable carriers can be employed. For example, an oral liquid preparation such as a suspended medicament or a syrup medicament can be prepared using water, sugars such as sucrose, sorbitol, fructose, etc.; glycols such as polyethylene glycol, propylene glycol, etc.; oils such as sesame oil, olive oil, soybean oil, etc.; antiseptics such as alkyl p-hydroxybenzoate, etc.; and flavors such as strawberry flavor, peppermint flavor, etc. Powders, pills, capsules and tablets can be prepared using excipients such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc.; surfactants such as fatty acid esters, etc.; plasticizers such as glycerine, and the like. Tablets and capsules are the most useful, oral unit dosage forms because of easy administration. To prepare tablets and capsules, solid pharmaceutical carriers are employed.

Further a solution for injection can be prepared using distilled water, a salt solution, a glucose solution or a carrier composed of a mixture of salt solution and a glucose solution.

It is desired that Compound (I) or salts thereof be administered in a dose of 150 to 400 mg/adult (approximately 60 kg)/day and that the number of administration be approximately 3 times per day for oral route. For parenteral route, it is preferred that the compound be administered in a dose of 50 to 150 mg/adult (approximately 60 kg)/day, depending upon necessity.

Hereafter the embodiments of the present invention are shown by referring to Examples below.

Physicochemical properties of the products obtained in the Examples are shown in Table 2.

EXAMPLE 1

In 400 ml of methylene chloride was dissolved 26.7 g of 11-(2-diethylaminoethylamino)-5,11-dihydro-6H-dibenz[b,e]azepin-6-one, and dry hydrogen chloride gas was blown into the solution with stirring. The reaction solution was concentrated under reduced pressure and 100 ml of acetonitrile was added to the residue. The mixture was heated at reflux for an hour. After allowing the mixture to stand at room temperature, precipitated crystals were separated by filtration to give 28.02 g of 3-(2-aminophenyl)-2-(2-diethylaminoethyl)isoindolin-1-one dihydrochloride 0.25 hydrate (Compound 1').

EXAMPLE 2

In 50 ml of ethyl alcohol was dissolved 1.75 g of 11-(3-dimethylaminopropylamino)-5,11-dihydro-6H-dibenz[b,e]azepin-6-one, and dry hydrogen chloride gas was blown into the solution with stirring. The obtained solution was concentrated under reduced pressure and the residue was dissolved in 50 ml of methyl alcohol. The solution was heated at reflux for 8 hours. The reaction mixture was concentrated to dryness under reduced pressure. The obtained solid was treated in ethyl ether and separated by filtration to give 1.83 g of 3-(2-aminophenyl)-2-(2-dimethylaminipropyl)isoindolin-1-one dihydrochloride 0.5 methyl alcohol dihydrate (Compound 2').

EXAMPLE 3

In 50 ml of methyl alcohol was dissolved 2.0 g of 11-(3-dimethylaminopropylamino)-5,11-dihydro-5H-dibenz[b,e]azepin-6-one. The solution was treated in the same manner as in Example 2 to give 1.12 g of 3-(2-aminophenyl)-2-(3-diethylaminopropyl)isoindolin-1-one dihydrochloride dihydrate (Compound 3').

EXAMPLE 4

3-(2-Aminophenyl)-2-(4-diethylaminobutyl)isoindolin-1-one dihydrochloride was obtained from 3.31 g of 11-(4-diethylamino-butylamino)-5,11-dihydro-6H-dibenz[b,e]azepin-6-one in the same manner as in Example 3. The dihydrochloride was dissolved in 100 ml of water and pH of the solution was adjusted to 11.0, and 100 ml of methylene chloride was added to the solution. After shaking, the aqueous layer was discarded and the organic layer was washed with saturated aqueous sodium chloride solution. After drying over anhydrous sodium sulfate, the organic layer was concentrated to dryness under reduced pressure.

The crude crystals obtained were recrystallized from toluene to give 1.34 g of 3-(2-aminophenyl)-2-(4-diethylaminobutyl)isoindolin-1-one (Compound 4).

EXAMPLE 5

The same procedure as in Example 1 were repeated except for using 3.39 g of 11-(3-butylaminopropylamino)-5,11-dihydro-6H-dibenz[b,e]azepin-6-one as the starting material. Thus, 3.03 g of 2-(3-dibutylaminopropyl)-3-(2-aminophenyl)isoindolin- 1-one monohydrochloride dihydrate (Compound 5') was obtained.

EXAMPLE 6

To 100 ml of a tetrahydrofuran solution containing 6.29 g of N-isopropylethylenediamine and 6.23 g of triethylamine was added 10.0 g of 11-chloro-5,11-dihydro-6H-dibenz[b,e]azepin-6-one under ice cooling. After stirring for an hour under ice cooling and for 5 hours at room temperature, the reaction mixture was concentrated under reduced pressure. The residue was dissolved in 200 ml of methylene chloride and 200 ml of water, and pH of the solution was adjusted to 2.0 with 4N-hydrochloric acid. After shaking, the organic layer was discarded and 200 ml of methylene chloride was added to the aqueous layer. The pH was adjusted to 11.5 with 10N-sodium hydroxide solution. After shaking, the aqueous layer was discarded.

After the organic layer was washed with saturated aqueous sodium chloride solution, the organic layer was dried over anhydrous sodium sulfate and concentrated under reduced pressure. The crude product obtained was subjected to silica gel column chromatography (eluting solvent, ethyl acetate:triethylamine=100:3). A fraction eluted earlier was concentrated to dryness under reduced pressure to give 7.62 g of 3-(2-aminophenyl)-2-(2-isopropylaminoethyl)isoindolin-1-one (Compound 6).

To 100 ml of a tetrahydrofuran solution of 7.62 g of the resulting Compound 6 was added 100 ml of a tetrahydrofuran solution of 2.86 g of fumaric acid. The mixture was stirred under ice cooling. Separation of the precipitated crystals by filtration gave 8.85 g of 3-(2-aminophenyl)-2-(2-isopropylaminoethyl)isoindolin-1-one monofumarate (Compound 6').

EXAMPLE 7

To a solution of 5.82 g of Compound 1, 2.16 g of paraformaldehyde and 2 mg of phenol red in 130 ml of methyl alcohol was added 1.51 g of sodium cyanoborohydride under ice cooling while stirring. While adjusting pH to about 6 by dropwise adding 3N-hydrogen chloride methyl alcohol solution thereto, the mixture was stirred at room temperature overnight and then concentrated under reduced pressure. The residue was dissolved in 150 ml of water and 150 ml of methylene chloride, and pH of the solution was adjusted to 11 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (eluting solvent, ethyl acetate:hexane:triethylamine=5:5:1). A fraction eluted earlier was concentrated under reduced pressure to give 1.75 g of 2-(2-diethylaminoethyl)-3-(2-dimethylaminphenyl)isoindolin-1-one (Compound 8). By concentrating a fraction eluted later under reduced pressure, 2.84 g of 2-(2-diethylaminoethyl)-3-(2-methylaminophenyl)isoindolin-1-one (Compound 7) was obtained.

EXAMPLE 8

The same procedures as in Example 7 were repeated except for using 1.68 g of Compound 1, 1.15 g of acetaldehyde and 0.44 g of sodium cyanoborohydride as the starting materials. Thus, 1.32 g of 2-(2-diethylaminoethyl)-3-(2-ethylaminophenyl)isoindolin-1-one (Compound 9) was obtained.

EXAMPLE 9

The same procedure as in Example 7 were repeated except for using 1.62 g of Compound 1, 0.72 g of butylaldehyde and 0.20 g of sodium cyanoborohydride as starting materials. Thus, 1.79 g of 3-(2-butylaminophenyl)-2-(2-diethylaminoethyl)isoindolin-1-one (Compound 10) was obtained.

EXAMPLE 10

The same procedure as in Example 1 were repeated except for using 1.25 g of 2-chloro-11-(2-diethylaminoethylamino)-5,11-dihydro-6H-dibenz[b,e]azepin-6-one as the starting material. Thus, 1.17 g of 3-(2-amino-5-chlorophenyl)-2-(2-diethylamino-ethyl)isoindolin-1-one dihydrochloride 0.5 hydrate (Compound 11') was obtained.

EXAMPLE 11

The same procedures as in Example 7 were repeated except for using 7.16 g of Compound 11, 2.40 g of paraformaldehyde and 1.68 g of sodium cyanoborohydride as the starting materials. Thus, 3.02 g of 3-(5-chloro-2-dimethylaminophenyl)-2-(2-diethylaminoethyl)isoindolin-1-one (Compound 13) and 3.23 g of 3-(5-chloro-2-methylaminophenyl)-2-(2-diethylaminoethyl)isoindolin-1-one (Compound 12) were obtained.

EXAMPLE 12

The same procedures as in Example 7 were repeated except for using 5.37 g of Compound 11, 2.64 g of acetaldehyde and 1.68 g of sodium cyanoborohydride as the starting materials. Thus, 3.27 g of 3-(5-chloro-2-ethylaminophenyl)-2-(2-diethylaminoethyl)isoindolin-1-one (Compound 14) was obtained.

EXAMPLE 13

The same procedures as in Example 7 were repeated except for using 5.37 g of Compound 11, 3.24 g of butylaldehyde and 0.94 g of sodium cyanoborohydride as the starting materials. Thus, 4.85 g of 3-(5-chloro-2-butylaminophenyl)-2-(2-diethylaminoethyl)isoindolin-1-one (Compound 15) was obtained.

EXAMPLE 14

To a solution of 7.45 g of Compound 1 in 50 ml of methylene chloride was added 2.59 g of acetic anhydride. The mixture was stirred at room temperature for 6 hours. To the reaction mixture was added 50 ml of water, and the pH was adjusted to 11.5 with 10N-sodium hydroxide solution. After shaking, the aqueous layer was discarded and the organic layer was washed with saturated aqueous sodium chloride solution. After drying over anhydrous sodium sulfate, the organic layer was concentrated to dryness under reduced pressure. The crude crystals obtained were recrystallized from acetonitrile to give 5.65 g of 3-(2-acetamidophenyl)-2-(2-diethylaminoethyl)-isoindolin-1-one (Compound 16).

EXAMPLE 15

The same procedures as in Example 3 were repeated except for using 2.40 g of 11-(2-diethylaminoethylamino)-1,4-dimethyl-5,11-dihydro-6H-dibenz[b,e]azepin-6-one as the starting material. The obtained crude crystals were recrystallized from isopropyl alcohol-isopropyl ether to give 1.77 g of 3-(2-amino-3,6- dimethylphenyl)-2-(2-diethylaminoethyl)-isoindolin-1-one dihydrochloride 0.33 hydrate (Compound 17′).

EXAMPLE 16

To a solution of 1.28 g of N,N,N′,N′-tetramethylethylene-diamine in 25 ml of tetrahydrofuran was added 10.5 ml of 1.05 M cyclohexane solution of sec-butyl lithium under a nitrogen gas atmosphere, and a solution of 1.77 g of N,N-diethylbenzamide in 15 ml of tetrahydrofuran was added to the solution at −78° C. After stirring for 10 minutes at −78° C., a solution of 2.24 g of 4-dimethylaminobenzaldehyde in 10 ml of tetrahydrofuran was added to the mixture. After stirring at −78° C. for 1.5 hours, the temperature was gradually elevated to 5° C. and the reaction mixture was concentrated under reduced pressure. To the residue were added 50 ml of water and 50 ml of ethyl ether, and pH of the mixture was adjusted to 0.5 with 4N-hydrochloric acid. After shaking, the organic layer was discarded and 50 ml of methylene chloride was added to the aqueous layer. The pH was adjusted to 12 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (eluting solvent, ethyl acetate:hexane:triethylamine=50:50:5). A fraction eluted secondly was concentrated under reduced pressure and the concentrate was tritylated with methyl alcohol to give 0.54 g of 3-(4-dimethylaminophenyl)-1,3-dihydro-isobenzofuran-1-one (Compound A).

Solid, IR spectrum (KBr. disk, cm$^{-1}$): 2900, 1745, 1620, 1535, 1370, 1300, 1290, 1070, 945, 815, 760, 720.

NMR spectrum (δppm, CDCl$_3$): 2.90 (s, 6H), 6.27 (s, 1H), 6.43–8.04 (m, 8H)

A fraction eluted thirdly was concentrated under reduced pressure to give 0.71 g of N,N-diethyl-2-[1-hydroxy-1-(4-dimethylaminophenyl)-methyl]benzamide (Compound B).

Oily, IR spectrum (neat): 3370, 1615, 1520, 1440, 1350, 805.

NMR spectrum (δppm, CDCl$_3$): 0.60–1.40 (m, 6H), 2.86 (s, 6H), 2.85–3.77 (m, 4H), 3.20–3.62 (m, 1H), 5.71 (brs, 1H), 6.44–7.69 (m, 8H)

To a solution of 0.32 g of Compound A and 1.41 g of Compound B in 10 ml of N,N-diethylethylenediamine was added 0.15 g of anhydrous zinc chloride. After heating at reflux for 2.5 hours in a nitrogen gas atmosphere, the mixture was concentrated under reduced pressure. To the residue were added 15 ml of methylene chloride and 50 ml of water, and pH of the mixture was adjusted to 1 with 4N-hydrochloric acid. After shaking, the organic layer was discarded and 30 ml of methylene chloride was added to the aqueous layer. The pH was adjusted to 12 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The residue was subjected to silica gel column chromatography (eluting solvent, ethyl acetate:hexane:triethylamine=10:20:1). A major fraction was concentrated under reduced pressure to give 1.13 g of 2-(2-diethylaminoethyl)-3-(4-dimethylaminophenyl)isoindolin-1-one (Compound 18).

EXAMPLE 17

The same procedures as in Example 16 were repeated except for using 6.39 g of N,N,N′,N′-tetramethylethylenediamine, 53 ml of 1.05M cyclohexane solution of sec-butyl lithium, 8.86 g of N,N-diethylbenzamide and 9.75 g of 4-diethylaminobenzaldehyde. Thus, 10.06 g of N,N-diethyl-2-[1-hydroxy-1-(4-diethylaminophenyl)-methyl]benzamide (Compound C) was obtained.

Solid, IR spectrum (KBr disk, cm$^{-1}$): 3400, 2970, 2930, 1615, 1520, 1435, 1355, 1260, 780.

NMR spectrum (δppm, CDCl$_3$): 0.93 (t, 6H), 1.10 (t, 6H), 3.31 (q, 4H), 2.41–3.72 (m, 4H), 5.77 (brs, 1H), 6.59–7.12 (q, 4H, AB type), 6.93–7.74 (m,4H).

Using 3.54 g of Compound C, 0.15 g of anhydrous zinc chloride and 5 ml of N,N-diethylethylenediamine, the same procedures as in Example 16 were repeated. The crude crystals obtained were crystallized from hexane to give 2.38 g of 2-(2-diethylaminoethyl)-3-(4-diethylaminophenyl)isoindolin-1-one (Compound 19).

Example 18

To a tetrahydrofuran solution of magnesium 1-naphthylbromide prepared from 1.22 g of metallic magnesium and 10.35 g of α-bromonaphthalene in 50 ml of tetrahydrofuran was added a solution of 6.16 g of N-(2-diethylaminoethyl)-phthalimide in 10 ml of tetrahydrofuran under ice cooling. After stirring for 2 hours under ice cooling, the mixture was concentrated under reduced pressure. To the residue were added 6.61 g of ammonium sulfate, 100 ml of ethyl ether and 100 ml of water. After shaking, the aqueous layer was discarded and 100 ml of water was added to the organic layer. The pH was adjusted to 1.5 with 4N-hydrochloric acid. After shaking, the organic layer was discarded and 100 ml of ethyl ether was added to the aqueous layer. The pH was adjusted to 11.5 with 10N-sodium hydroxide solution. After shaking, the aqueous layer was discarded. After the organic layer was washed with saturated aqueous sodium chloride solution, the organic layer was dried over anhydrous sodium sulfate and concentrated to dryness under reduced pressure. The crude crystals obtained were recrystallized from diisopropyl ether to give 2.85 g of 2-(2-diethylaminoethyl)-3-hydroxy-3-(1-naphthyl)isoindolin-1-one (Compound 20).

Example 19

To a solution of 0.11 mole of butyl lithium in 68 ml of hexane and 150 ml of tetrahydrofuran was added a solution of 15.80 g of 3-bromopyridine in 20 ml of tetrahydrofuran at −78° C. After stirring for 30 minutes at −78° C., a solution of 24.63 g of N-(2-diethylaminoethyl)phthalimide in 30 ml of tetrahydrofuran was added to the mixture. After stirring at −78° C. for 1 hour, a solution of 6.61 g of acetic acid in 30 ml of tetrahydrofuran was added, and the mixture was concentrated under reduced pressure. To the residue were added 300 ml of water and 300 ml of ethyl ether, and pH of the mixture was adjusted to 1.5 with 4N-hydrochloric acid. After shaking, the organic layer was discarded and 200 ml of methylene chloride was added to the aqueous layer. The pH was adjusted to 10 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (ethyl acetate:triethylamine=20:1). A major fraction was concentrated under reduced pressure to give 16.99 g of 2-(2-diethylaminoethyl)-3-hydroxy-3-(3-pyridyl)isoindolin-1-one (Compound 21).

Example 20

To a solution of 2.03 g of Compound 21 and 20 mg of imidazole in 30 ml of tetrahydrofuran was added to 0.37 g (purity, 60%) of sodium hydride under ice cooling. After heating at reflux for 15 minutes in a nitrogen gas atmosphere, 2 ml of carbon disulfide was added thereto, followed by heating at reflux for 30 minutes. Under ice cooling, 0.97 g of methyl iodide was added and the mixture was stirred for 30 minutes under ice cooling. After allowing the mixture to stand at room temperature overnight, 2 ml of acetic acid was added and the mixture was concentrated under reduced pressure. To the residue were added 100 ml of methylene chloride and 100 ml of water, and pH of the mixture was adjusted to 8 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (eluting solvent, ethyl acetate:hexane:triethylamine=10:10:1). A major fraction was concentrated under reduced pressure to give 1.67 g of 2-(2-diethylaminoethyl)-3-[(methylthio)thiocarbonyloxy]-3-(2-pyridyl)isoindolin-1-one as an oily substance.

With heating at reflux, a solution of 1.44 g of the previously obtained oily substance in 30 ml of xylene was added to a solution of 1.51 g of tributyl tin in 40 ml of xylene. After heating at reflux for 4 hours, the mixture was concentrated under reduced pressure. To the obtained crude product were added 50 ml of ethyl ether and 50 ml of water, and the pH was adjusted to 3 with 4N-hydrochloric acid.

After shaking, the orgaic layer was discarded and 30 ml of methylene chloride was added to the aqueous layer. The pH was adjusted to 12 with 10N-sodium hydroxide solution. After shaking, the aqueous layer was discarded. After the organic layer was washed with saturated aqueous sodium chloride solution, the organic layer was dried over anhydrous sodium sulfate and concentrated under reduced pressure. The crude product obtained was subjected to silica gel column chromatography (eluting solvent, ethyl acetate:triethylamine=10:1). A fraction eluted secondly was concentrated under reduced pressure to give 0.40 g of 2-(2-diethylaminoethyl)-3-(3-pyridyl)isoindolin-1-one (Compound 22).

Example 21

The same procedures as in Examples 19 were repeated except for using 15.80 g of 2-bromopyridine in place of 3-bromopyridine. The obtaned crude crystals were recrystallized from toluene-hexane to give 17.77 g of 2-(2-diethylaminoethyl)-3-hydroxy-3-(2-pyridyl)isoindolin-1-one (Compound 23).

Example 22

The same procedures as in Example 20 were repeated except for using 4.88 g of Compound 23 in place of Compound 21. Thus, 0.20 g of 2-(2-diethylaminoethyl)3-(2-pyridyl)-isoindolin-1-one (Compound 24) was obtained.

Example 23

To a solution of 1.35 g of 11-(2-diethylaminoethylamino)-4-methyl-5, 11-dihydro-6H-dibenz[b,e]azepin-6 -one in 50 ml of methyl alcohol was added 5 ml of 3N-hydrogen chloride methyl alcohol solution. After stirring at room temperature for an hour, the reaction mixture was concentrated to dryness under reduced pressure. The obtained solid was tritylated with isopropyl ether and then separated by filtration to give 1.91 g of 3-(2-amino-3-methylphenyl)-2-(2-diethylaminoethyl)isoindolin-1one dihydrochloride 0.6 hydrate (Compound 25').

Example 24

The same procedures as in Example 23 were repeated except for using 1.76 g of 11-(2-diethylaminoethylamino)2, 4-dimethyl-5, 11-dihydro-6H-dibenz[b,e]azepin-6-one as the starting material. Thus, 2.03 g of 3-(2-amino-3, 5-dimethylphenyl)-2-(2-diethylaminoethyl)isoindolin-1-one dihydrochloride dihydrate (Compound 26') was obtained.

Example 25

Procedures similer to Example 16 were repeated except for using 6.39 g of N,N,N', N'-tetramethylethylenediamine, 8.86 g of N,N-diethylbenzamide and 12.32 g of 2-(2-diethylaminoethyl)phthalimide as the starting materials. Thus, 8.63 g of a mixture of 3-(N,N-diethylcarbamoylphenyl)-2-(2-diethylaminoethyl)-3-hydroxy-isoindolin-1-one (Compound 29) and spiro[2-(2-diethylaminoethyl)isoindolin-3-one-1,1'-1', 3'-dihydroisobenzofuran-3'-one] (Compound 30) was obtained.

By treating 6.21 g of the mixture described above with diisopropyl ether, 4.32 g of Compound 29 was obtained.

Example 26

To a solution of 1.68 g of the mixture of Compound 29 and Compound 30 in 10 ml of methyl alcohol solution was added 5 ml of 3N-hydrogen chloride methyl alcohol solution. After stirring at room temperature for an hour, the mixture was concentrated under reduced pressure. To the residue were added 50 ml of water and 50 ml of ethyl ether. After shaking, the organic layer was discarded and 50 ml of methylene chloride was added to the aqueous layer. The pH was adjusted to 12 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (eluting solvent, ethyl acetate:hexane:triethylamine=10:10:1). A major fraction was concentrated under reduced pressure and the resulting crude crystals were purified by recrystallization from cyclohexane to give 0.88 g of spiro[2-(2-diethylaminoethyl)isoindolin-3-one-1, 1'-1', 3'-dihydroisobenzofuran-3'-one] (Compound 30).

Example 27

To a solution of 2.18 g of Compound 29 in 25 ml of acetic acid was added 5 g of zinc powders activated by washing with 2N-hydrochloride. After heating at reflux for 3.5 hours, the mixture was filtered and concentrated under reduced pressure. To the residue was added 20 ml of water, and pH was adjusted to 7 with 10N-sodium chloride solution. Then, filtration was performed and the mother liquor was concentrated under reduced pressure. The residue was subjected to HP-10 high porous polymer column-column chromatography (eluting solvent, water:methyl alcohol=1:3). A major fraction was concentrated to dryness under reduced pressure to give 1.56 g of 2-[2-(2-diethylaminoethyl)isoindolin-1-on-3-yl]benzoic acid (Compound 27).

Example 28

To a solution of 0.53 g of Compound 27 in 5 ml of methyl alcohol was added 0.2 ml of conc. sulfuric acid. After heating at reflux for 2 hours, pH was adjusted to 7 with sodium hydrogencarbonate. The mixture was concentrated under reduced pressure. After 30 ml of water and 30 ml of methylene chloride were added to the residue, pH was adjusted to 12 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure to give 0.14 g of methyl 2-[2-(2-diethylaminoethyl)isoindolin-1-on-3-yl]benzoate (Compound 28).

Example 29

To a solution of 2.50 g of 2-cyano-11-hydroxy-5, 11-dihydro-6H-dibenz[b,e]azepin-6-one and 1.78 g of pyridine in 40 ml of methylene chloride was added 1.78 g of thionyl chloride under ice cooling. The mixture was stirred for an hour and ice cooling and then at room temperature for 30 minutes. The reaction solution was added to a solution of 5.81 g of N,N-diethylethylenediamine in 50 ml of methylene chloride at −5° to 0° C. with stirring. After stirring for an hour under ice cooling, 5 ml of water was added thereto. Further 200 ml of methylene chloride and 100 ml of water were added to the reaction mixture, and pH was adjusted to 1 with 4N-hydrochloric acid. After shaking, the organic layer was discarded and 200 ml of methylene chloride was added to the aqueous layer. The pH was adjusted to 10 with 10N-sodium hydroxide solution. After shaking, the aqueous layer was discarded and the organic layer was washed with saturated aqueous sodium chloride solution. After drying over anhydrous sodium sulfate, the organic layer was concentrated under reduced pressure. The crude product obtained was subjected to silica gel column chromatography (eluting solvent, ethyl acetate:hexane:triethylamine=16:4:1). A major fraction was concentrated to dryness under reduced pressure to give 1.42 g of 3-(2-amino-5-cyanophenyl)-2-(2-diethylaminoethyl)isoindolin-1-one (Compound 31).

Example 30

The same procedures as in Example 29 were repeated except for using 5.01 g of 2-cyano-11-hydroxy-5, 11-dihydro-6H-dibenz[b,e]-azepin-6-one and 12.82 g of 2-(aminoethyl)-1-ethylpyrrolidine as the starting materials. Thus, 0.93 g of 3-(2-amino-5-cyanophenyl)-2-[1-ethylpyrrolidin-2-yl) methyl]isoindolin-1-one (Compound 35) was obtained.

Example 31

The same procedures as in Exaple 29 were repeated except for using 5.00 g of 2-cyano-11-hydroxy-5, 11-dihydro-6H-dibenz[b,e]-azepin-6-one and 10.22 g of 2-isopropylaminoethylamine as the starting materials. Thus, 0.71 g of 3-(2-amino-5-cyanophenyl)-2-(2-isopropylaminoethyl)isoindolin-1-one (Compound 36) was obtained.

Example 32

The same procedures as in Example 29 were repeated except for using 20 g of 2-cyano-11-hydroxy-5, 11-dihydro-6H-dibenz[b,e]azepin-6-one and 42 ml of N-ethylethylenediamine as the starting materials. Thus, 3-(2-amino-5-cyanophenyl)-2-(2-ethylaminoethyl)isoindolin-1-one (Compound 38) was obtained. After dissolving it in isopropanol, Compound 38 was treated with hydrogen chloride-ethanol solution and the solution was concentrated to dryness under reduced pressure. The obtained solid was crystallized from acetonitrile to give 2.3 g of 3-(2-amino-5-cyanophenyl)-2-(2-ethylaminoethyl)isoindolin-1-one dihydrochloride (Compound 38').

Example 33

Tablet:
Tablets having the following composition were prepared in a conventional manner.
Compound 31', 20 mg
Lactose, 60 mg
Potato starch, 30 mg
Polyvinyl alcohol, 2 mg
Magnesium stearate, 1 mg
Pigment, trace

Example 34

Powder:
Powders having the following composition were prepared in a conventional manner.
Compound 1', 20 mg
Lactose, 280 mg

Example 35

Injection:
Distilled water for injection was added to 100 ml of Compound 11' until total volume becomes 20 ml. Subsequently, the mixture was treated in a conventional manner to prepare an injection.

Reference Example 1

To a solution of 15.9 g of phenyldichloroborane in 100 ml of dichloromethane were dropwise added 12.12 g of 2, 4-dimethylaniline and 25.3 g of triethylamine under cooling at −30° C. while stirring. The mixture was stirred for an hour under ice cooling. To the obtained solution 16.42 g of orthophthaldehydic acid methyl ester was dropwise added, while cooling at −40° C. with stirring. After stirring for an hour under ice cooling, the reaction mixture was allowed to stand overnight. To the resulting solution was added 100 ml of water, and extraction was carried out at pH of 3. The extracted organic layer was washed with saturated aqueous sodium bicarbonate solution and with saturated aqueous sodium chloride solution. After drying over anhydrous sodium sulfate, the organic layer was filtered and the resulting filtrate was concentrated to dryness under reduced pressure. To the obtained solid was added to ether, and the solid was ground into powders. Thus, 23.05 g of 3-(2-amino-3, 5-dimethylphenyl)-1, 3-dihydroisobenzofuran-1-one was obtained.

Light yellowish white powders, IR (KBr disk, $cm^{-1}$): 1750, 1480, 1283, 1064, 750.

Melting point: 114°–116° C.

In 300 ml of methyl alcohol was dissolved 22.45 g of 3-(2-amino-3, 5-dimethylphenyl)-1, 3-dihydroisobenzofuran-1-one. The solution was heated at reflux for 10 hours in the presence of 20.23 g of p-toluenesulfonic acid monohydrate. The resulting solution was concentrated to dryness under reduced pressure. The obtained solid was dissolved in 200 ml of dichloromethane. The solution was washed with saturated aqueous sodium bicarbonate solution and with saturated aqueous sodium chloride solution. After drying over anhydrous sodium sulfate, the solution was filtered and the resulting filtrate was concentrated to dryness under reduced pressure. To the obtained solid was added to diisopropyl ether and the solid was ground into powders. Thus, 12.65 g of 2,4-dimethyl-11-methoxy-5, 11-dihydro-6H-dibenz[b,e]azepin-6-one was obtained.

White powders, IR (KBr disk, cm$^{-1}$): 1640, 1367, 1115, 1080, 730.

Melting point: 197.5°–199° C.

To a solution of 5.35 g of the compound described above in 25 ml of dichloromethane was added 3.45 g of acetyl chloride. While stirring the mixture under ice cooding, 0.81 ml of methyl alcohol was dropwise added, and the mixture was stirred for an hour under ice cooling. Stirring was further continued at room temperature overnight. The obtained solution was concentrated to dryness under reduced pressuer. The obtained solid was added to a solution of 11.62 g of N,N-diethylethylenediamine in 100 ml of tetrahydrofuran under cooling with stirring, followed by stirring for an hour under ice cooling. To the obtained solution were added 50 ml each of water and dichloromethane. The pH was adjusted to 3 and subsequently to 10. The mixture was washed with saturated aqueous sodium chloride solution. After drying over anhydrous sodium sulfate, the solution was filtered and the resulting filtrate was concentrated to dryness under reduced pressure. To the obtained solid was added diisopropyl ether and the solid was ground into powders. The obtained solid was recrystallized from toluene to give 2.28 g of 11-(2-diethylaminoethylamino), 2, 4-dimethyl-5, 11-dihydro-6H-dibenz[b,e]azepin-6-one.

Ir(KBr disk, cm$^{-1}$): 2960, 1647, 1452, 1365, 760, 730.

Melting point: 135°–136° C.

NMR (DMSO-d$_6$, δppm): 0.86 (t, 3H), 0.98 (t, 3H), 2.20–2.25 (s, 6H), 2.20–2.45 (m, 4H), 2.66 (s, 2H), 4.40–5.01 (s, 1H), 6.85 –6.91 (s, 1H), 7.00–7.07 (s, 1H), 7.21–7.70 (m, 4H), 9.56–9.90 (s, 1H).

Elemental analysis:
Calcd: C=75.18 (%) H=8.32 N=11.95 Found: C=75.05 H=8.44 N=11.84

What is claimed:

1. An isoindolin-1-one compound represented by the formula (I):

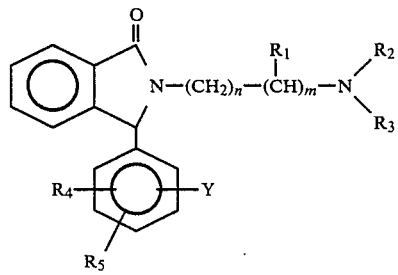

wherein n represents an integer of 1 to 6; m represents 0 or 1, $R_1$, $R_2$ and $R_3$ are each independently hydrogen or lower alkyl, or when m is 1, $R_1$ and one of $R_2$ and $R_3$ form a pyrrolidine ring; Y represents carboxyl, lower alkoxycarbonyl, carbamoyl, N,N-lower alkylsubstituted carbamoyl or amino represented by the formula:

wherein $R_6$ and $R_7$ are each independently hydrogen, lower alkyl or lower alkanoyl; $R_4$ and $R_5$ are each independently hydrogen, lower alkyl, cyano or halogen; and a pharmaceutically acceptable acid addition alt or metal salt thereof.

2. A compound according to claim 1, wherein n is 2, 3 or 4; and m is 0.

3. A compound according to claim 1 wherein $R_2$ and $R_3$ are each independently hydrogen or $C_{1-6}$ alkyl.

4. A compound according to claim 3, wherein one of $R_2$ and $R_3$ is hydrogen; and the other is $C_{1-6}$ alkyl.

5. A compound according to claim 4, wherein $C_{1-6}$ alkyl is methyl or ethyl.

6. A compound to claim 3, wherein both of $R_2$ and $R_3$ are $C_{1-6}$ alkyl.

7. A compound to claim 6, wherein $C_{1-6}$ alkyl is methyl or ethyl.

8. A compound according to claim 1, wherein Y is bound at 2-position of phenyl ring, and is a member selected from the group consisting of carboxyl and the amino represented by the formula

9. A compound according to claim 8, wherein both of $R_6$ and $R_7$ are hydrogen.

10. A compound according to claim 1, wherein, one of $R_4$ and $R_5$ is bound at 5-position of phenyl ring, and is a member selected from the group consisting of hydrogen, cyano and halogen; and the other is hydrogen.

11. A compound according to claim 2, wherein both of $R_2$ and $R_3$ are $C_{1-6}$ alkyl; and Y is bound at 2-position of phenyl ring and represents carboxyl or amino.

12. A compound according to claim 2, wherein both of $R_2$ and $R_3$ are $C_{1-6}$ alkyl; and one of $R_4$ and $R_5$ is bound at 5-position of phenyl ring and represents hydrogen, cyano or halogen; and the other is hydrogen.

13. A compound according to claim 1, wherein n is 2, m is 0, both of $R_2$ and $R_3$ are ethyl, and Y is 2-amino.

14. A compound according to claim 1, wherein n is 2, m is 0, both of $R_2$ and $R_3$ are ethyl, Y is 2-amino, one of $R_4$ and $R_5$ is 5-chloro and the other is hydrogen.

15. A compound according to claim 1, wherein n is 2, m is 0, both of $R_2$ and $R_3$ are ethyl, Y is 2-amino, one of $R_4$ and $R_5$ is 5-cyano and the other is hydrogen.

16. A compound according to claim 1, wherein n is 2, m is 0, one of $R_2$ and $R_3$ is ethyl, the other is hydrogen Y is 2-amino, one of $R_4$ and $R_5$ is 5-cyano and the other is hydrogen.

17. A pharmaceutical composition comprising a pharmaceutical carrier and, as an antiarrhythmic active ingredient, an effective amount of an isoindolin-1-one compound defined in claim 1.

* * * * *